United States Patent [19]

Karrer et al.

[11] Patent Number: 5,114,977

[45] Date of Patent: May 19, 1992

[54] ETHERS

[75] Inventors: Friedrich Karrer, Zofingen; Alfred Rindlisbacher, Muttenz, both of Switzerland

[73] Assignee: Ciba-Geigy Corporation, Ardsley, N.Y.

[21] Appl. No.: 740,657

[22] Filed: Aug. 2, 1991

Related U.S. Application Data

[63] Continuation of Ser. No. 403,254, Sep. 5, 1989, abandoned.

[30] Foreign Application Priority Data

Sep. 15, 1988 [CH] Switzerland ................ 3444/88

[51] Int. Cl.$^5$ ............... A01N 31/14; C07C 43/285; C07C 43/29
[52] U.S. Cl. ........................... 514/720; 568/637
[58] Field of Search ............... 568/637; 514/720

[56] References Cited

U.S. PATENT DOCUMENTS

| | | | |
|---|---|---|---|
| 4,057,587 | 11/1977 | Karrer | 260/613 |
| 4,115,456 | 9/1978 | Gante | 568/637 |
| 4,123,556 | 10/1978 | Karrer | 260/613 |
| 4,141,921 | 2/1979 | Karrer | 568/636 |
| 4,196,215 | 4/1980 | Gante | 514/564 |
| 4,550,192 | 10/1985 | Rodgers | 560/62 |

FOREIGN PATENT DOCUMENTS 2205096 11/1988 United Kingdom .

OTHER PUBLICATIONS

F. Karrer and S. Faroog, Some Insect Growth . . . Biological Properties, Scientific Papers of the Institute of Organic and Physical Chemistry of Wroclaw Technical Univ., 22 (7), pp. 289-302 (1981).
Patent Abstract of Japan 11 (43), (C-402) 2490 JP61-207352, ATSUJI KITAJIMA, (Feb. 1987).
M. Boehm et al., J. Labelled Compds., XXV(9), pp. 1007-1015 (Sep. 6, 1988).

*Primary Examiner*—Marianne Cintins
*Assistant Examiner*—Margaret Argo
*Attorney, Agent, or Firm*—Marla J. Mathias; Edward McC. Roberts

[57] ABSTRACT

There are disclosed 1-[4-(halophenoxy)phenoxy]-4-pentines of formula

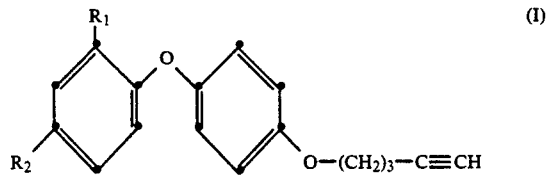

(I)

wherein $R_1$ and $R_2$ are each independently of the other chloro or fluoro and one of $R_1$ and $R_2$ is also hydrogen, a process for their preparation and intermediates for their preparation, the use of these compounds in pest control, and pesticidal compositions which contains a compound of formula I as active component. The preferred field of use is ovicidal control of pests.

8 Claims, No Drawings

ETHERS

This application is a continuation of application Ser. No. 403,254, filed Sep. 5, 1989, now abandoned.

The present invention relates to 1-[4-(halophenoxy)-phenoxy]-4-pentines, to the preparatioin thereof and to intermediates for their preparation, and to the use of these compounds in pest control.

The compounds of this invention have the formula I

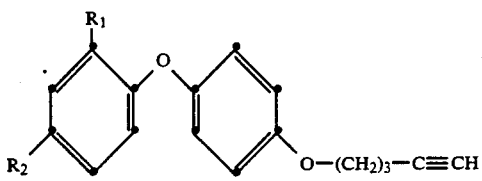

wherein $R_1$ and $R_2$ are each independently of the other chlorine or fluorine and one of $R_1$ and $R_2$ can also be hydrogen.

Among the compounds of formula I, the monofluoro and difluoro compounds as well as the monochloro and dichloro compounds are preferred for use in pest control.

Preferred individual compounds are:
1-[4-(4-fluorophenoxy)phenoxy]-4-pentine,
1-[4-(2-fluorophenoxy)phenoxy]-4-pentine, and
1-[4-(2,4-difluorophenoxy)phenoxy]-4-pentine.

Substituted phenoxy-4-pentines are disclosed as acaricides in U.S. patent specification 2,304,962. However, this reference does not specify any individual compounds from among the 1-[4-(monohalophenoxy)-phenoxy]-4-pentines also covered by the definition. Finally, German Offenlegungsschrift 2 305 698 discloses substituted phenoxy-2-pentines, and German Offenlegungsschrift 2 547 146 discloses substituted (4-phenoxyphenoxyalkyl)(alkynyl) ethers and thioethers with acaricidal properties.

These compounds, however, have not proved satisfactory in all respects as regards their acaricidal and, especially, ovicidal activity.

It is the object of the present invention to provide further acaricides with improved activity.

Surprisingly, it has been found that the novel compounds of formula I have an improved acaricidal, especially ovicidal, activity as compared with the compounds of the prior art.

The ovicidal activity of the compounds of formula I against aphids, specifically against Dysaphis plantaginea, Aphis pomi and Dysaphis brancoi.

The compounds of formula I can be prepared by reacting a 4-(halophenoxy)phenolate of formula II, wherein $R_1$ and $R_2$ are as defined for formula I and M is an alkali metal or alkaline earth metal, with a 1-halo-4-pentine of formula III, wherein $R_3$ is chloro, bromo or iodo:

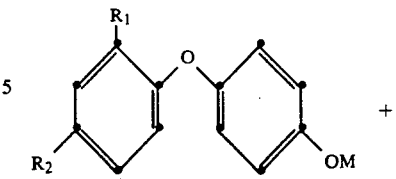

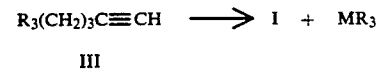

in an inert solvent and in the temperature range from $-10°$ C. to $+140°$ C.

It is preferred to carry out the process in the presence of an alkali metal iodide in a polar aprotic solvent, for example dimethyl sulfoxide, sulfolane or a dialkyl amide such as dimethyl formamide, in the temperature range from 0° to 80° C., and $R_3$ is chloro.

The present invention also relates to the process for the preparation of the compounds of formula I.

The intermediate 4-(2,4-difluorophenoxy)phenol can be prepared by reacting 4-(2,4-difluorophenoxy)anisole with an aqueous hydrohalic acid, preferably 30-50% hydrobromic acid or hydriodic acid, in the temperature range from 80°-130° C., preferably from 100°-110° C., and preferably in glacial acetic acid as solvent.

The invention also relates to the novel 4-(2,4-difluorophenoxy)phenol and to the preparation thereof.

The phenolate of formula II can be prepared from the 4-(2,4-difluorophenoxy)phenol and a suitable base, for example an alkali metal hydroxide or alkaline earth metal hydroxide, an alkali metal alcoholate or alkaline earth metal alcoholate, an alkali metal hydride or alkaline earth metal hydride or, finally, sodium or potassium carbonate, by known methods, and, if desired, isolated.

The starting materials of formulae II and III are known and, where they are novel, can be prepared by known methods.

The compounds of this invention are valuable pesticides while being well tolerated by warm-blooded animals and by plants. The compounds of formula I are therefore suitable e.g. for controlling pests of animals and plants. Such pests belong principally to the phylum of Arthropoda, such as in particular insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera and arachnids of the order Acarina, e.g. mites and ticks, especially the fruit tree red spider mite (Panonychus ulmi), as well as aphids. Every development stage of the pests can be controlled, i.e. the adults, pupae and nymphs, and also in particular the larvae and, preferably, the eggs. It is thus possible to control effectively in particular larvae and eggs of phytopathogenic insect pests and mites in crops of ornamentals and useful plants, for example in vegetable and cotton crops and, in particular, in fruit crops. The control of preimaginal stages of phytopathogenic insects is to be singled out for special invention. If compounds of formula I are ingested by imagines, then a direct kill of the pests or a reduced oviposition and/or hatching rate can be observed.

For the control of pests that are parasites of animals, especially of domestic animals and productive livestock, ectoparasites such as mites and ticks, and Diptera such as Lucilia sericata, are of particular interest.

The good pesticidal activity of the compounds of formula I corresponds to a mortality of at least 50–60% of the above pests.

The compounds of this invention are of particular interest for controlling fruit tree red spider mites of the genus Panonychus, in particular of the species Panonychus ulmi.

The conventional method in agricultural practice of controlling this pest, the eggs of which winter in the fruit trees and the first generation of which causes particularly severe damage to fruit crops, comprises spraying ovicidal compositions of the prior art in a concentration of 50 g/100 l on the cultivated plant before flower formation and, after this treatment, controlling the pests in the mobile development stages 2 to 3 weeks later with other suitable pesticides.

In contradistinction thereto, the compounds of this invention, when sprayed in a concentration of only 30 g/100 l before flower formation, afford comprehensive protection against the fruit tree red spider mite for a period of over six weeks and thus effect almost total kill of the pests.

The compounds of formula I have an exceedingly broad activity. Their ovicidal activity is very pronounced against the fruit tree red spider mite as well as against the rosy apple aphid.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The compounds of formula I are used in unmodified form, or preferably together with the inert, agriculturally acceptable adjuvants conventionally employed in the art of formulation, and can therefore be formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Further suitable surfactants are also the fatty acid methyl taurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyl bis(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or a combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients for obtaining special effects.

EXAMPLES

PREPARATION OF THE ACTIVE SUBSTANCES AND OF THE INTERMEDIATES p1: Preparation of 4-(2,4-difluorophenoxy)anisole

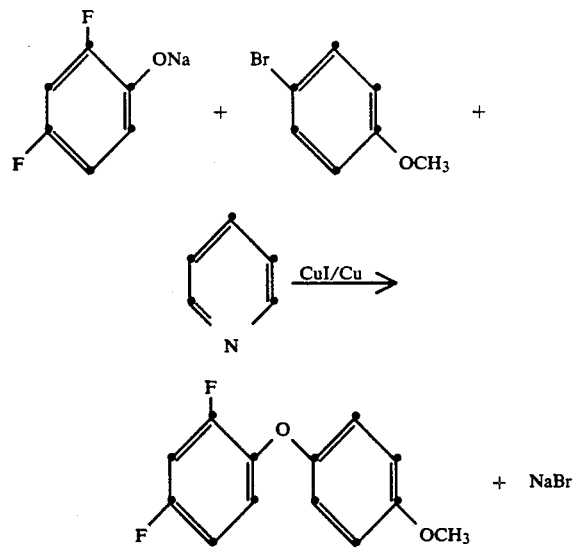

To a suspension of the anhydrous sodium salt of 206 g of 2,4-difluorophenol in 400 ml of diethylene glycol dimethyl ether are added 5 g of copper powder, 5 g of copper(I) iodide, 8 ml of pyridine and 393 g of 4-bromoanisole. With stirring, the reaction mixture is heated, under nitrogen, for 17 hours to 150°–155° C. After cooling, the reaction mixture is filtered over Hyflo and the bulk of the solvent is removed by vacuum distillation. The residue is dissolved in ether and the ethereal solution is washed repeatedly with 10% aqueous sodium hydroxide and then with water. The ethereal solution is dried over sodium sulfate and the solvent is removed by distillation. The residue is purified by chromatography over silica gel (eluant: 8:1 mixture of petroleum ether/diethyl ether). The solvent is removed by evaporation, to give the title compound in the form of a residual oil; $n_D^{22} = 1.5466$.

P2: Preparation of 4-(2,4-difluorophenoxy)phenol

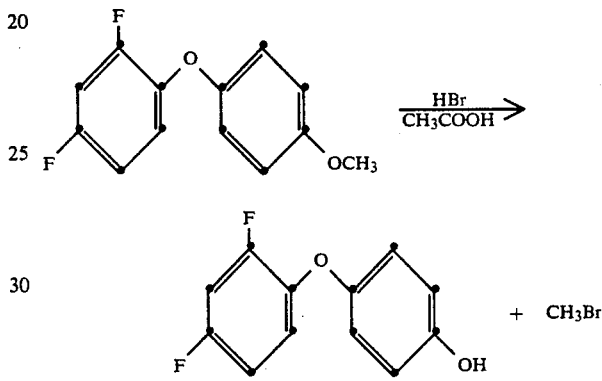

With stirring, 170 g of the 4-(2,4-difluorophenoxy)anisole obtained according to Example P1, 500 ml of 48% hydrobromic acid and 400 ml of glacial acetic acid are heated for 20 hours to ca. 105° C. After working up, the crude 4-(2,4-difluorophenoxy)phenol is purified by chromatography over silica gel (eluant: 1:4 mixture of diethyl ether/n-hexane) as well as by subsequent recrystallisation from diethyl ether/petroleum ether. The purified title compound has a melting point of 82°–84° C.

P3: Preparation of the active substance 1-[4-(2,4-difluorophenoxy)phenoxy]-4-pentine (compound 1 of Table 1)

With cooling, a solution of 4.2 g of potassium tert-butoxide in 20 ml of anhydrous dimethyl sulfoxide is added to a solution of a 8 g of 4-(2,4-difluorophenoxy)-phenol in 20 ml of anhydrous dimethyl sulfoxide and 0.3 g of finely powdered potassium iodide. With stirring, a solution of 4,4 g of 1-chloro-4-pentine in 5 ml of dimethyl sulfoxide is added dropwise at 10°–15° C. to the above mixture. After 2 hours the reaction mixture is warmed to room temperature (20°–23° C.) and stirred for 24 hours at this temperature. The reaction mixture is then poured into ice-water and extracted repeatedly with a 1:2 mixture of diethyl ether/hexane. The combined organic phases are washed until neutral with cold 10% aqueous sodium hyroxide and then with water and dried over sodium sulfate. The solvent is removed by vacuum distillation and the residue is further purified by chromatography over silica gel 60 (eluant: 1:9 mixture of diethyl ether/n-hexane), affording the pure 1-[4-(2,4- difluorophenoxy)-phenoxy]-4-pentine with a refractive index $n_D^{22} = 1.5392$.

Further compounds of formula I, for example

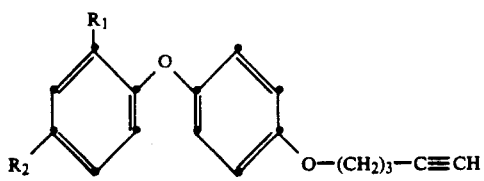

were prepared in accordance with the above Examples.

TABLE 1

| Compound | R₁ | R₂ | Phys. data |
|---|---|---|---|
| 1. | F | F | $n_D^{20}$: 1.5392 |
| 2. | H | F | $n_D^{20}$: 1.5505 |
| 3. | F | H | $n_D^{20}$: 1.5530 |
| 4. | H | Cl | m.p.: 37–38° C. |
| 5. | Cl | H | |
| 6. | Cl | Cl | $n_D^{21}$: 1.5785 |
| 7. | Cl | F | |
| 8. | F | Cl | |

Formulation of compounds of formula I according to Table 1 (throughout, percentages are by weight)

| F1: Emulsifiable concentrates | a) | b) |
|---|---|---|
| a compound according to Table 1 | 10% | 25% |
| calcium dodecylbenzenesulfonate | — | 5% |
| castor oil polyethylene glycol ether (36 mol of ethylene oxide) | 25% | 5% |
| tributylphenol polyethylene gylcol ether | — | 40% |
| cyclohexanone | — | 40% |
| butanol | 15% | — |
| xylene mixture | — | 25% |
| ethyl acetate | 50% | — |

Emulsions of any required concentration can be produced from such concentrates by dilution with water.

| F2: Solutions | a) | b) |
|---|---|---|
| a compound according to Table 1 | 10% | 5% |
| polyethylene glycol 400 | 70% | — |
| N-methyl-2-pyrrolidone | 20% | 20% |
| epoxidised coconut oil | — | 1% |
| petroleum distillate (boiling range 160–190° C.) | — | 74% |

These solutions are suitable for application in the form of microdrops.

| F3: Granulates | a) | b) |
|---|---|---|
| a compound according to Table 1 | 5% | 10% |
| kaolin | 94% | — |
| highly dispersed silicic acid | 1% | — |
| attapulgite | — | 90% |

The active ingredient or ingredients is or are dissolved in methylene chloride, the solution is sprayed onto the carrier, and the solvent is subsequently evaporated off in vacuo.

| F4: Extruder granulates | |
|---|---|
| a compound according to Table 1 | 10% |

| F4: Extruder granulates (continued) | |
|---|---|
| sodium lignosulfonate | 2% |
| carboxymethylcellulose | 1% |
| kaolin | 87% |

The active ingredient or ingredients is or are mixed and ground with the adjuvants, and the mixture is subsequently moistened with water. The mixture is extruded and then dried in a stream of air.

| F5: Coated granulate | |
|---|---|
| a compound according to Table 1 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| F6: Dusts | a) | b) | c) | d) |
|---|---|---|---|---|
| a compound according to Table 1 | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient and, optionally, grinding the mixture in a suitable mill.

| F7: Wettable powders | a) | b) | c) |
|---|---|---|---|
| a compound according to Table 1 | 20% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 67% | 27% | — |

The active ingredient is thoroughly mixed with the adjuvants and the mixture is thoroughly ground in a suitable mill, affording wettable powders which can be diluted with water to give suspensions of the desired concentration.

| F8: Suspension concentrate | |
|---|---|
| a compound according to Table 1 | 40% |
| ethylene glycol | 10% |
| nonylphenol polyethylene glycol (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

Biological Tests

B1: Action against *Aëdes aegypti*

A concentration of 12.5 ppm is obtained by pipetting a specific amount of a 0.1% solution of the test compound in acetone onto the surface of 150 ml of water in a beaker. After the acetone has evaporated, 30 to 40 two-day old larvae of *Aëdes aegypti* are put into the beaker containing the test compound. Mortality counts are made after 2 and 7 days.

Compounds of Table 1 exhibit good activity in this test.

B2: Action against *Spodoptera littoralis* and *Heliothis virescens* (larvae and eggs)

Three cotton plants each having a height of about 15-20 cm and grown in pots are treated with a sprayable liquid formulation of the test compound. After the spray coating has dried, the potted plants are placed in a metal container having a capacity of about 20 liters and covered with a glass plate. The humidity in the interior of the covered container is regulated such that no water of condensation forms. Direct light falling on the plants is avoided. The three plants are then infested altogether with:
a) 50 larvae of *Spodoptera littoralis* or *Heliothis virescens* in the $L_1$-stage;
b) 20 larvae of *Spodoptera littoralis* or *Heliothis virescens* in the $L_3$-stage;
c) 2 egg deposits of *Spodoptera littoralis* or *Heliothis virescens*. (The procedure is that two leaves of each plant are put into a plexiglass cylinder sealed at both ends with gauze. Two egg deposits of Spodoptera, or a part of a cotton leaf with eggs of Heliothis deposited thereon, are added to the leaves sealed in the cylinder.)

Evaluation in comparison with untreated controls is made after 4 to 5 days on the basis of the following criteria:
a) the number of still living larvae,
b) inhibition of larval development and moulting,
c) feeding damage (shredding and perforation damage),
d) hatching rate (number of larvae hatched from the eggs).

In this test, compounds of Table 1 exhibit good overall activity at a concentration of 400 ppm.

B3: Ovicidal action against *Spodoptera littoralis*

Eggs of *Spodoptera littoralis* deposited on filter paper are cut out of the paper and immersed in a 0.05% by weight solution of the test compound in a 1:1 mixture of acetone-water. The treated egg deposits are then removed from this mixture and kept in plastic dishes at 28° C. and 60% relative humidity. The hatching rate, i.e. the number of larvae which have developed from the treated eggs, is determined after 5 days.

Compounds of Table 1 exhibit good activity in this test.

B4: Action against *Laspeyresia pomonella* (eggs)

Egg deposits of *Laspeyresia pomonella* not more than 24 hours old are immersed on filter paper for 1 minute in an aqueous acetonic solution containing 400 ppm of the test compound.

After the solution has dried, the filter paper and the eggs are placed in petri dishes and kept at a temperature of 28° C. The percentage of larvae hatched from the treated eggs is evaluated after 6 days.

Compounds of Table 1 exhibit good activity in this test.

B5: Ovicidal action against *Heliothis virescens* and *Spodoptera littoralis*

Appropriate amounts of a wettable powder formulation containing 25% by weight of the test compound are mixed with sufficient water to produce an aqueous emulsion with an active ingredient concentration of 400 ppm. One-day-old egg deposits of Heliothis on cellophane and of Spodoptera on paper are immersed in these emulsions for 3 minutes and then collected by suction on round filters. The treated deposits are placed in petri dishes and kept in the dark at 28° C. and 60% relative humidity. The hatching rate, i.e. the number of larvae which have developed from the treated eggs, in comparison with untreated controls, is determined after 5 to 8 days.

In this test, compounds of Table 1 exhibit an 80 to 100% ovicidal activity (mortality) against *Heliothis virescens* and *Spodoptera littoralis*.

B6: Comparison of the compounds of the invention with those of the prior art with respect to ovicidal action against *Panonychus ulmi*

Compounds 1, 2 and 3 are tested with the following comparison compounds of the prior art.

| Compound | Formula | Reference |
|---|---|---|
| A | phenyl-O-phenyl-O-(CH$_2$)$_3$-C≡CH | DE-OS 2 304 962 |
| B | F-phenyl-O-phenyl-O-CH$_2$-C≡CH | DE-OS 2 305 698 |

| Compound | Formula | Reference |
|---|---|---|
| C | (structure) | DE-OS 2 305 698 |

Structure C: diphenyl ether with O—CH$_2$—C≡CH substituent.

Method of determining the ovicidal action against *Panonychus ulmi*

Discs measuring 5 cm in diameter are punched from apple leaves. These discs are laid on moist cotton wool in a plastic petri dish. Then 7 adult females of *Panonychus ulmi* are placed on each disc and left for 48 hours for oviposition. Application of the test compounds is made after removal of the females. The discs are sprayed with a hand atomizer until a fine coating of droplets has formed on them. Two dishes are treated with each test compound at concentrations of 50 and 25 mg of active substance per liter. After the spray coatings have dried, the dishes are covered, kept at 25° C. and, 6 days after application, the percentage of non-hatched eggs is determined (ovicidal action). Three replicates are carried out at intervals of 4 weeks.

Comparison of ovicidal action:

TABLE 2

| Active compound | Conc. mg/l | Ovicidal action in % |
|---|---|---|
| A (prior art) | 50 | 72 |
|  | 25 | 61 |
| B (prior art) | 50 | 67 |
|  | 25 | 32 |
| C (prior art) | 50 | 71 |
|  | 25 | 43 |
| 1 (Table 1) | 50 | 100 |
|  | 25 | 98 |
| 2 (Table 1) | 50 | 88 |
|  | 25 | 67 |
| 3 (Table 1) | 50 | 93 |
|  | 25 | 78 |

B7: Action against the eggs of *Dysaphis plantaginea* and of *Dysaphis brancoi* in a field test Winter eggs of *Dysaphis plantaginea* and *Dysaphis brancoi* (roses apple aphids) are sprayed with a spray mixture containing 30 g of active compound per 100 l in the open.

Evaluation of hatched and developing aphids is made one month after this application, based on the total number of eggs. The percentage of hatched and developing aphids determined after treatment with compounds 1, 2 and 3 at a uniform rate of application of 450 g/ha is:

*Dysaphis plantaginea* = 10%
*Dysaphis brancoi* = 4%

B8: Action against eggs of *Aphis pomi* (green apple aphid) in a laboratory test Pieces of apple branch 10 cm long (2-year-old wood from winter pruning) which are infested with winter eggs of A. pomi are immersed for 1 minute in a spray mixture of test compound containing 30 g of active substance per 100 l. The treated pieces are kept for 4 weeks in air-permeable test containers at 22° C. and 60–80% relative humidity. The hatching rate of the treated eggs is determined by examination under a stereoscopic microscope. Compounds 1, 2 and 3 effect an ovicidal action of >80% against *Aphis pomi.*

What is claimed is:

1. A 1-[4-(halophenoxy)phenoxy]-4-pentine of formula I

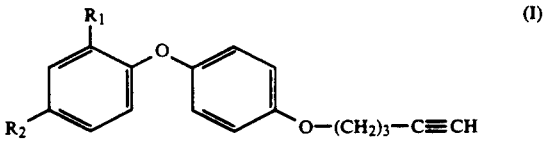

wherein $R_1$ and $R_2$ are each independently of the other hydrogen or fluoro with the proviso that $R_1$ and $R_2$ are not simultaneously hydrogen.

2. A 1-[4-(4-fluorophenoxy)phenoxy]-4-pentine according to claim 1.

3. A 1-[4-(2-fluorophenoxy)phenoxy]-4-pentine according to claim 1.

4. A 1-[4-(2,4-difluorophenoxy)phenoxy]-4-pentine according to claim 1.

5. A pesticidal composition which comprises an effective amount of a 1-[4-(halophenoxy)phenoxy]-4-pentine or mixture of 1-[4-(halophenoxy)phenoxy]-4-pentines of formula I

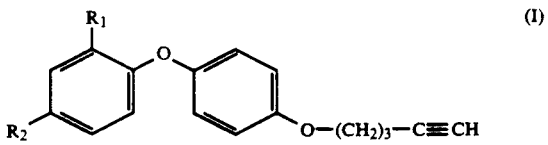

wherein $R_1$ and $R_2$ are each independently of the other hydrogen or fluoro with the proviso that $R_1$ and $R_2$ are not simultaneously hydrogen.

6. A pesticidal composition according to claim 5, which comprises 1-[4-(4-fluorophenoxy)phenoxy]-4-pentine.

7. A pesticidal composition according to claim 5, which comprises 1-[4-(2-fluorophenoxy)phenoxy]-4-pentine.

8. A pesticidal composition according to claim 5, which comprises 1-[4-(2,4-difluorophenoxy)phenoxy]-4-pentine.

* * * * *